(12) United States Patent
Eskridge

(10) Patent No.: US 11,266,435 B2
(45) Date of Patent: *Mar. 8, 2022

(54) STENT RETRIEVER HAVING AN EXPANDABLE FRAGMENT GUARD

(71) Applicant: Joe Michael Eskridge, Clyde Hill, WA (US)

(72) Inventor: Joe Michael Eskridge, Clyde Hill, WA (US)

( * ) Notice: Subject to any disclaimer, the term of this patent is extended or adjusted under 35 U.S.C. 154(b) by 222 days.

This patent is subject to a terminal disclaimer.

(21) Appl. No.: 16/724,065

(22) Filed: Dec. 20, 2019

(65) Prior Publication Data

US 2020/0121355 A1    Apr. 23, 2020

Related U.S. Application Data

(63) Continuation-in-part of application No. PCT/US2017/061685, filed on Nov. 15, 2017, which
(Continued)

(51) Int. Cl.
*A61B 17/221*     (2006.01)
*A61B 17/22*      (2006.01)
(Continued)

(52) U.S. Cl.
CPC .... *A61B 17/320725* (2013.01); *A61B 17/221* (2013.01); *A61F 2/95* (2013.01);
(Continued)

(58) Field of Classification Search
CPC .... A61F 2/0103; A61F 2/0105; A61F 2/0108; A61F 2/013; A61F 2/014;
(Continued)

(56) References Cited

U.S. PATENT DOCUMENTS 4,762,129 A    8/1988  Bonzel
4,794,931 A    1/1989  Yock
(Continued)

FOREIGN PATENT DOCUMENTS

EP    1645242 A2    4/2006
EP    1955661       8/2008
(Continued)

OTHER PUBLICATIONS

Machi Paolo et al. Solitaire FR thrombectomy system: immediate results in 56 1-22 consecutive acute ischemic stroke patients. J Neurointervent Surg 2012; 4(1):pp. 62-66, procedure, fig. 1,2.
(Continued)

*Primary Examiner* — Wade Miles
(74) *Attorney, Agent, or Firm* — Timothy E. Siegel Patent Law, PLLC; Timothy E. Siegel

(57) ABSTRACT

A stent retriever assembly having a proximal end and a distal end and including a mesh tube having a distal and proximal end and being connected to a first wire. Also, a blood-porous fragment guard is at the distal end of the mesh tube and has a central hub and extending radially and proximally from the central hub. Further, a second wire is connected to the central hub, and when this second wire is pulled proximally relative to the first wire, the hub is pulled proximally, which thereby causes the fragment guard to deploy in expanded form.

5 Claims, 4 Drawing Sheets

Related U.S. Application Data is a continuation of application No. 15/627,806, filed on Jun. 20, 2017, now Pat. No. 9,848,906.

(51) Int. Cl.
- *A61B 17/3207* (2006.01)
- *A61F 2/95* (2013.01)
- *A61F 2/01* (2006.01)

(52) U.S. Cl.
CPC ........... *A61B 2017/2212* (2013.01); *A61B 2017/22034* (2013.01); *A61B 2017/22081* (2013.01); *A61B 2017/320741* (2013.01); *A61F 2002/016* (2013.01)

(58) Field of Classification Search
CPC .... A61B 2017/2212; A61B 2017/2217; A61B 2017/22034; A61B 2017/22035; A61B 2017/22081; A61B 17/221; A61B 17/22031
See application file for complete search history.

(56) References Cited

U.S. PATENT DOCUMENTS

| | | | |
|---|---|---|---|
| 4,932,413 A | 6/1990 | Sbockey | |
| 5,160,321 A | 11/1992 | Sahota | |
| 5,254,088 A | 10/1993 | Lundquist et al. | |
| 5,509,900 A | 4/1996 | Kirkman | |
| 5,571,173 A | 11/1996 | Perodi | |
| 5,735,289 A | 4/1998 | Pfeffer et al. | |
| 5,827,324 A | 10/1998 | Cassell | |
| 6,010,517 A | 1/2000 | Baccaro | |
| 6,059,822 A | 5/2000 | Kenesaka et al. | |
| 6,142,987 A * | 11/2000 | Tsugita | A61F 2/013 604/500 |
| 6,283,991 B1 | 9/2001 | Cox et al. | |
| 6,309,399 B1 | 10/2001 | Barbut | |
| 6,344,041 B1 | 2/2002 | Kupiecki et al. | |
| 6,371,972 B1 | 4/2002 | Wallace et al. | |
| 6,391,044 B1 | 5/2002 | Yadav et al. | |
| 6,540,722 B1 * | 4/2003 | Boyle | A61F 2/013 604/106 |
| 6,558,405 B1 * | 5/2003 | McInnes | A61F 2/013 606/200 |
| 6,652,556 B1 | 11/2003 | Van Tassel et al. | |
| 6,695,813 B1 * | 2/2004 | Boyle | A61F 2/01 604/106 |
| 6,712,766 B2 | 3/2004 | Harada | |
| 6,716,237 B1 * | 4/2004 | Alt | A61F 2/013 623/1.11 |
| 7,160,318 B2 | 1/2007 | Greenberg et al. | |
| 7,195,636 B2 | 3/2007 | Avellanet et al. | |
| 7,226,475 B2 | 6/2007 | Lenz et al. | |
| 7,621,928 B2 | 11/2009 | Thramann et al. | |
| 7,662,168 B2 | 2/2010 | McGuckin et al. | |
| 7,927,350 B2 | 4/2011 | Rabbitte | |
| 8,123,796 B2 | 2/2012 | Kasprzak | |
| 8,512,399 B2 | 8/2013 | Lafontaine | |
| 8,529,614 B2 | 9/2013 | Berez et al. | |
| 8,545,530 B2 | 10/2013 | Eskridge | |
| 8,551,132 B2 | 10/2013 | Eskridge et al. | |
| 8,556,930 B2 | 10/2013 | Ellingwood | |
| 8,668,729 B2 | 3/2014 | Kaufmann et al. | |
| 8,734,504 B2 | 5/2014 | Kelly | |
| 8,753,362 B2 | 6/2014 | Widomski et al. | |
| 8,814,925 B2 | 8/2014 | Hillaire | |
| 8,852,205 B2 * | 10/2014 | Brady | A61B 17/22031 606/114 |
| 8,876,863 B2 | 11/2014 | Eskridge | |
| 8,911,490 B2 | 12/2014 | Perkins et al. | |
| 9,402,708 B2 * | 8/2016 | Holloway | A61F 2/01 |
| 9,456,834 B2 * | 10/2016 | Folk | A61B 17/221 |
| 9,463,036 B2 | 10/2016 | Brady | |
| 9,848,906 B1 * | 12/2017 | Eskridge | A61B 17/221 |
| 2002/0004667 A1 * | 1/2002 | Adams | A61F 2/013 606/200 |
| 2002/0013616 A1 | 1/2002 | Carter et al. | |
| 2002/0022858 A1 * | 2/2002 | Demond | A61F 2/0105 606/200 |
| 2002/0026211 A1 * | 2/2002 | Khosravi | A61F 2/012 606/200 |
| 2002/0042626 A1 * | 4/2002 | Hanson | A61F 2/013 606/200 |
| 2002/0072730 A1 | 6/2002 | McGill et al. | |
| 2002/0103501 A1 * | 8/2002 | Diaz | A61F 2/013 606/200 |
| 2002/0107534 A1 | 8/2002 | Schaefer et al. | |
| 2002/0138133 A1 | 9/2002 | Lenz et al. | |
| 2002/0156457 A1 | 10/2002 | Fisher | |
| 2002/0165576 A1 * | 11/2002 | Boyle | A61B 17/221 606/200 |
| 2002/0165601 A1 | 11/2002 | Clerc | |
| 2003/0109917 A1 | 6/2003 | Rudin | |
| 2003/0163158 A1 * | 8/2003 | White | A61B 17/221 606/200 |
| 2004/0034386 A1 | 2/2004 | Fulton et al. | |
| 2004/0038460 A1 | 2/2004 | Scott | |
| 2004/0122466 A1 * | 6/2004 | Bales | 606/200 |
| 2004/0199197 A1 | 10/2004 | Eidenschink et al. | |
| 2005/0060017 A1 | 3/2005 | Fischell et al. | |
| 2005/0096735 A1 | 5/2005 | Hojeibane et al. | |
| 2005/0283182 A1 | 12/2005 | Pierce et al. | |
| 2006/0058834 A1 | 3/2006 | Do et al. | |
| 2006/0106421 A1 | 5/2006 | Teoh | |
| 2006/0135943 A1 | 6/2006 | Mandrusov et al. | |
| 2006/0224179 A1 | 10/2006 | Kuharczyk et al. | |
| 2006/0264905 A1 | 11/2006 | Eskridge et al. | |
| 2006/0271154 A1 | 11/2006 | Woodall | |
| 2006/0287668 A1 * | 12/2006 | Fawzi | A61F 2/0105 606/200 |
| 2007/0088387 A1 | 4/2007 | Eskridge et al. | |
| 2007/0191884 A1 | 8/2007 | Eskridge et al. | |
| 2007/0299461 A1 | 12/2007 | Elliott | |
| 2008/0004687 A1 | 1/2008 | Barbut et al. | |
| 2008/0039929 A1 | 2/2008 | Davis et al. | |
| 2008/0140051 A1 * | 6/2008 | Bei | A61F 2/011 604/509 |
| 2008/0243170 A1 | 10/2008 | Jenson et al. | |
| 2009/0024157 A1 | 1/2009 | Anukhin | |
| 2009/0082803 A1 | 3/2009 | Adams et al. | |
| 2009/0132024 A1 | 5/2009 | Berkhoff | |
| 2009/0171274 A1 | 7/2009 | Harlev et al. | |
| 2009/0192405 A1 | 7/2009 | Carney | |
| 2009/0292307 A1 | 11/2009 | Razack | |
| 2009/0326640 A1 | 12/2009 | Yoshimura et al. | |
| 2010/0042201 A1 | 2/2010 | Sherif | |
| 2010/0057019 A1 | 3/2010 | Zelenka | |
| 2010/0087850 A1 * | 4/2010 | Razack | A61B 17/32075 606/200 |
| 2010/0087908 A1 * | 4/2010 | Hilaire | A61F 2/01 623/1.11 |
| 2010/0234878 A1 | 9/2010 | Hruska et al. | |
| 2010/0280534 A1 | 11/2010 | Sher | |
| 2011/0040314 A1 | 2/2011 | McGuckin, Jr. et al. | |
| 2011/0040319 A1 * | 2/2011 | Fulton, III | A61F 2/013 606/194 |
| 2011/0046669 A1 | 2/2011 | Goraltchouk et al. | |
| 2011/0112614 A1 | 5/2011 | Haarer | |
| 2011/0118769 A1 | 5/2011 | Bliss et al. | |
| 2011/0125181 A1 | 5/2011 | Brady | |
| 2011/0137334 A1 | 6/2011 | Anderson et al. | |
| 2011/0160833 A1 | 6/2011 | Gonzalez et al. | |
| 2011/0190863 A1 * | 8/2011 | Ostroot | A61F 2/013 623/1.11 |
| 2011/0196414 A1 * | 8/2011 | Porter | A61F 2/012 606/200 |
| 2012/0046676 A1 | 2/2012 | Morsi | |
| 2012/0053596 A1 | 3/2012 | Gordon | |
| 2012/0071911 A1 | 3/2012 | Sadasivan et al. | |
| 2012/0130408 A1 | 5/2012 | Shur et al. | |
| 2013/0090682 A1 | 4/2013 | Bachman et al. | |

(56) References Cited

U.S. PATENT DOCUMENTS

| | | | |
|---|---|---|---|
| 2013/0197567 A1* | 8/2013 | Brady | A61B 17/221 606/200 |
| 2013/0204290 A1 | 8/2013 | Clarke et al. | |
| 2013/0345738 A1 | 12/2013 | Eskridge | |
| 2014/0005651 A1 | 1/2014 | Eskridge | |
| 2014/0074149 A1 | 3/2014 | Garcia et al. | |
| 2014/0094896 A1 | 4/2014 | Berez et al. | |
| 2014/0114342 A1 | 4/2014 | Berez et al. | |
| 2014/0121672 A1* | 5/2014 | Folk | A61B 17/221 606/127 |
| 2014/0172071 A1 | 6/2014 | Berez et al. | |
| 2014/0296889 A1* | 10/2014 | Avneri | A61B 17/320725 606/159 |
| 2015/0173782 A1 | 6/2015 | Garrison | |
| 2015/0313732 A1* | 11/2015 | Fulton, III | A61F 2/958 623/1.11 |
| 2016/0022291 A1* | 1/2016 | Johnson | A61B 8/12 606/113 |
| 2016/0120570 A1* | 5/2016 | Kobayashi | A61B 90/39 606/166 |
| 2016/0206426 A1* | 7/2016 | Khoynezhad | A61B 17/221 |
| 2017/0112513 A1* | 4/2017 | Marchand | A61F 2/014 |
| 2017/0112514 A1* | 4/2017 | Marchand | A61B 17/3415 |
| 2017/0119408 A1* | 5/2017 | Ma | A61M 25/0021 |
| 2017/0128089 A1* | 5/2017 | Ma | A61B 17/12177 |

FOREIGN PATENT DOCUMENTS

| | | |
|---|---|---|
| EP | 2308383 B1 | 6/2014 |
| RU | 2407466 C1 | 12/2010 |
| WO | 9000371 | 1/1990 |
| WO | 9825656 | 6/1998 |
| WO | 9956801 | 11/1999 |
| WO | 0128434 A1 | 4/2001 |
| WO | 0135839 A2 | 5/2001 |
| WO | 03099168 A2 | 12/2003 |
| WO | 2005037129 A1 | 4/2005 |
| WO | 2011106426 | 9/2011 |
| WO | 2012120490 | 9/2012 |
| WO | 2012167156 A1 | 12/2012 |
| WO | 2013109784 A1 | 7/2013 |
| WO | 2014047650 | 3/2014 |
| WO | 2016049529 | 3/2016 |

OTHER PUBLICATIONS

International Search Report and Written Opinion issued by ISA Australia Patent Office dated Mar. 7, 2018 for related PCT international application PCT/US2017/061685.

* cited by examiner

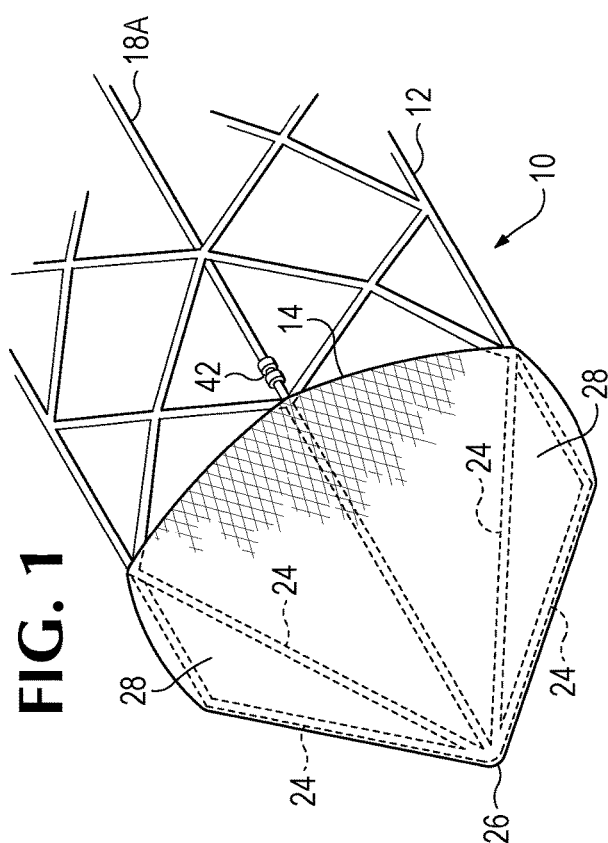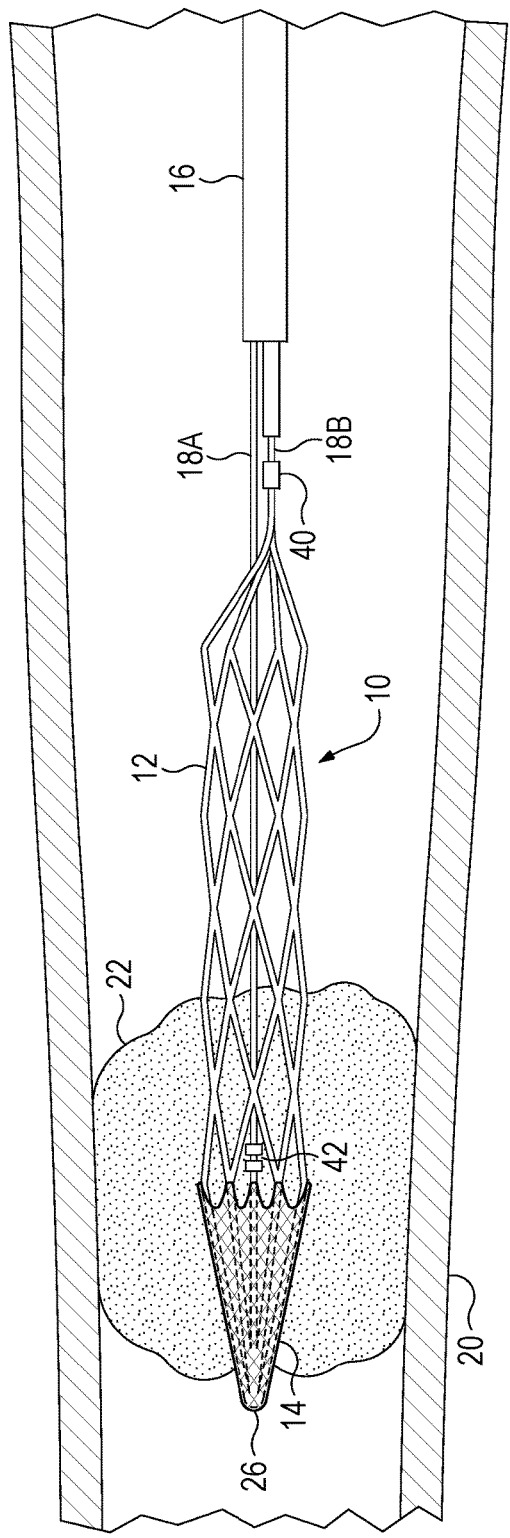

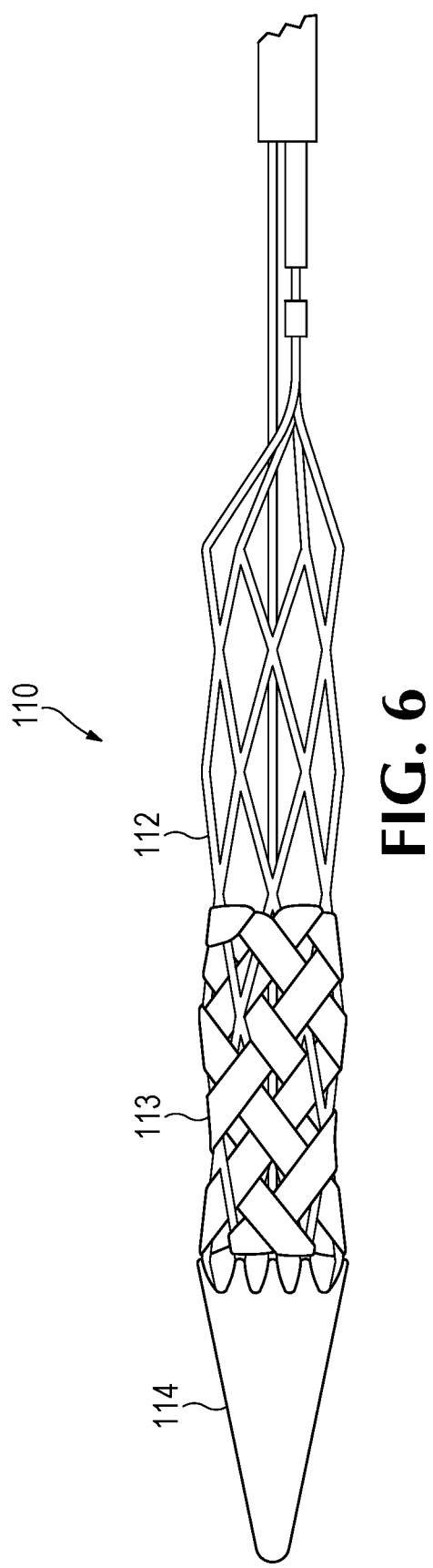

STENT RETRIEVER HAVING AN EXPANDABLE FRAGMENT GUARD

RELATED APPLICATIONS

This application is a continuation-in-part of international application PCT/US17/61685, filed Nov. 15, 2017, which itself is a continuation of U.S. application Ser. No. 15/627,806, filed Jun. 20, 2017, now U.S. Pat. No. 9,848,906, issued Dec. 26, 2017, both of which are incorporated by reference as if fully set forth herein.

TECHNICAL FIELD

The invention is in the technical field of devices for treating blood vessel clots, and more particularly devices for removing clots that block a cerebral artery, which are equipped with a blood porous fragment guard that prevents fragments of material from lodging in the cerebral artery.

BACKGROUND

The medical arts have advanced rapidly in the area of stroke treatment. Until recently, only medicinal treatment could be offered. Then, stents capable of retrieving the clot material blocking a blood vessel in an ischemic stroke were developed. Now, if a patient is seen quickly after onset the clot material can be swiftly removed, thereby saving a great deal of brain function, that would otherwise be lost.

Still, many challenges remain, in the removal of a clot that blocks a cerebral artery. One of these challenges is the tendency of fragments of material to break off of the clot as it is being removed, flow in the direction of blood flow, and lodge anew in some narrow cerebral artery, causing a secondary stroke, which can be damaging.

Notably, different types of clots have varying physical properties. Clots that form in the cerebral arteries, through an accumulation of material tend to have the consistency of gelatin. Some clots, however, form from material that has been deposited over time in the atria of the heart, and then breaks off (sometimes as the result of heart surgery) and travels to the cerebral arteries. This material has a consistency more similar to that of peanut butter. Finally, there are clots caused by material deposited in the aorta that breaks off and travels to the cerebral arteries. This material is typically harder than the material from the other two types of clots.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a stent retriever assembly having a proximal end and a distal end and including a mesh tube having a distal and proximal end and being connected to a first wire. Also, a blood-porous fragment guard is at the distal end of the mesh tube and has a central hub and extends radially and proximally from the central hub. Further, a second wire is connected to the central hub, and when this second wire is pulled proximally relative to the first wire, the hub is pulled proximally, which thereby causes the fragment guard to deploy in expanded form.

In a second separate aspect, the present invention may take the form of a method of removing a clot from an artery, that utilizes a stent retriever assembly having a proximal end and a distal end. This stent retriever has a mesh tube having a distal and proximal end and being connected to a first wire and a blood-porous fragment guard at the distal end of the mesh tube. This fragment guard includes a central hub and extends radially and proximally from the central hub. Further, a second wire is connected to the central hub, and when this second wire is pulled proximally relative to the first wire, the hub is pulled proximally, which thereby causes the fragment guard to deploy in expanded form. In the method, the stent retriever is moved to a proximal side of the clot and is pushed through the clot. Then the second wire is pulled relative to the first wire, thereby widening the fragment guard and the stent retriever is pulled proximally to pull material from the clot proximally.

In a third separate aspect, the present invention may take the form of a stent retriever catheter assembly having a proximal end and a distal end, and including a catheter, having a flexible tube sized to fit through the arterial system of a person, and to reach a blood clot in an artery. A first and second wire extend through the tube and a handle is connected to the first and second wires, which can be advanced and retracted with at least 1 cm of independence relative to each other. Further, a mesh tube having a distal and proximal end is connected at its proximal end to the first wire. Finally, a blood-porous fragment guard is at the distal end of the mesh tube, includes a central hub, and extends radially and proximally from the central hub. When the second wire is connected to the central hub, and is pulled proximally relative to the first wire, the hub is pulled proximally, which thereby causes the fragment guard to deploy in expanded form.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

FIG. 1 is an isometric view of a stent retriever according to the present invention.

FIG. 2 is a sectional view of an artery clogged by a clot, with the stent retriever of FIG. 1 piercing the clot.

FIG. 6 is an isometric view of an alternative embodiment of a catheter assembly, according to the present invention.

DETAILED DESCRIPTION OF THE PREFERRED EMBODIMENTS

Figure 3:
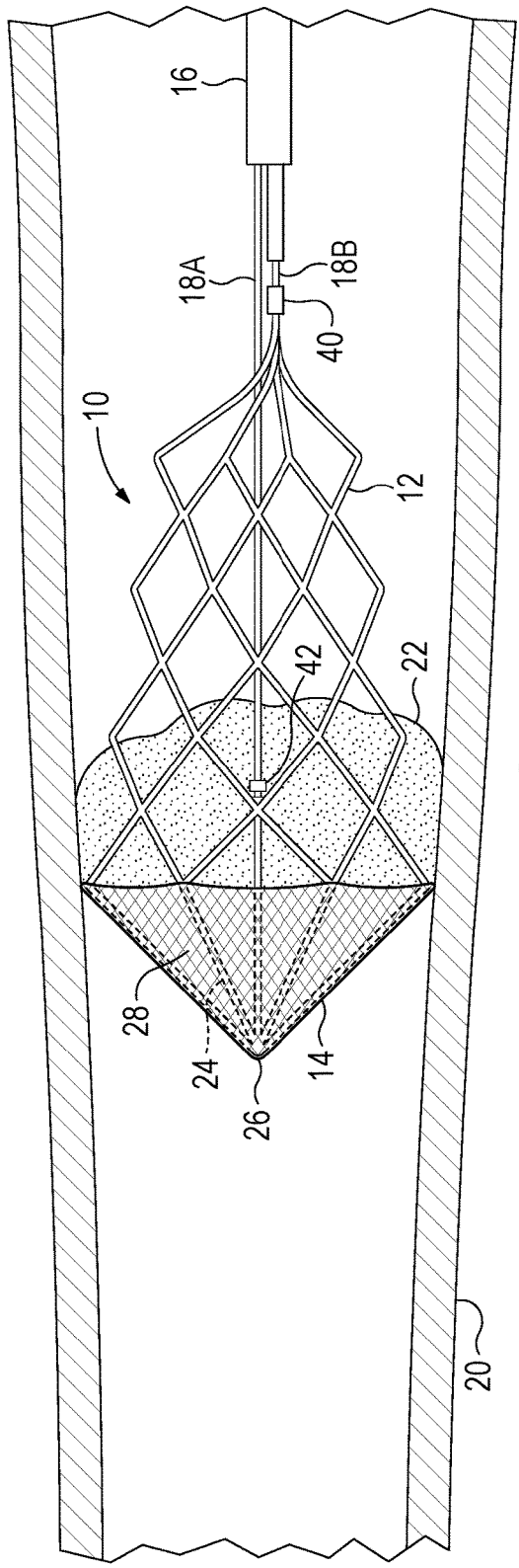
FIG. 3 is the sectional view of FIG. 2, with the stent retriever of FIG. 1 deployed.

Referring to FIGS. 1 and 2, in a preferred embodiment, a stent retriever 10 includes a wire mesh 12 (also referred to as a "mesh tube") and a woven fragment guard 14. It is controlled by a pair of wires 18A and 18B, which must be separately advanceable for the stent retriever 10 to work correctly. The stent retriever 10 is positioned in an artery 20, near a clot 22 by introduction of a catheter 16. After a distal end of catheter 16 is positioned near clot 22, the stent retriever 10 is deployed by pushing wires 18A and 18B forward. A system for permitting this action is shown and described in U.S. Pat. No. 8,876,863. After or during deployment the stent retriever 10 is pushed through clot 22, so that at least the fragment guard 14 is pushed all the way through.

Figure 4:
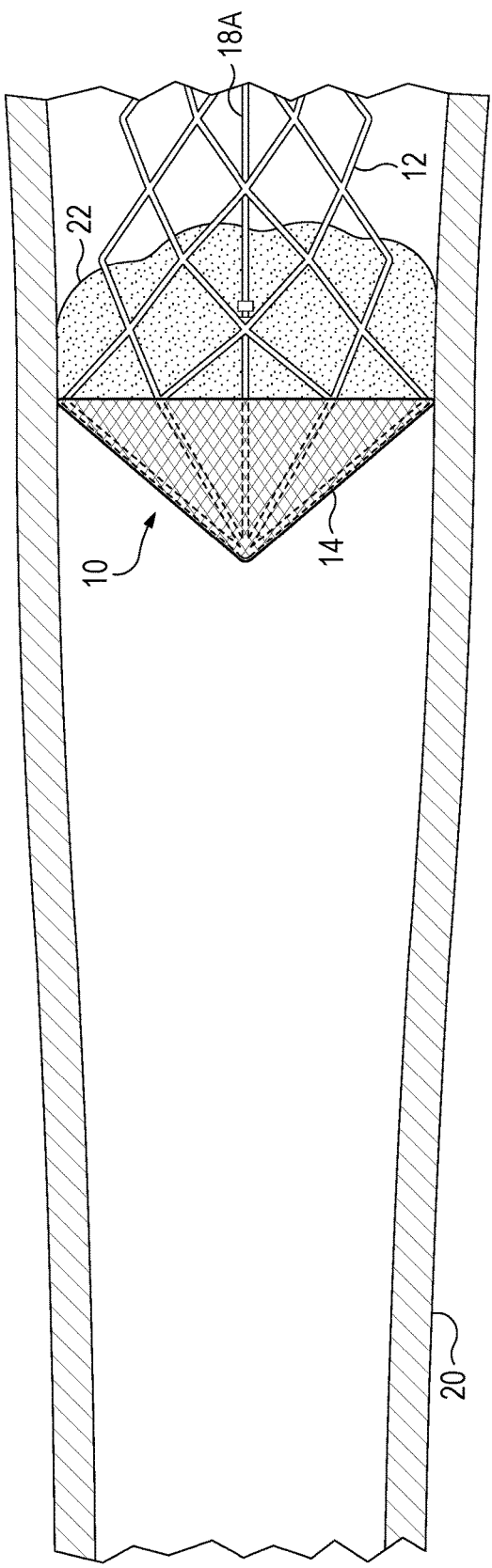
FIG. 4 is the sectional view of FIG. 2, with the stent retriever of FIG. 1 further expanded and in the process of removing the clot.

Referring also to FIG. 3, wire 18B is the advanced relative to wire 18A. Fragment guard 14 is made of a set of spokes 24 that meet in an apex 26 (also referred to as a "central hub"), and are all covered by a fabric 28. When wire 18B is advanced, or wire 18A is retracted, then spokes 24 are spread apart (much as the spokes of an umbrella). The stent retriever is now pulled proximally, bringing the clot 22 with it, and with fragment guard 14 protecting the artery 20 further on in the direction of blood flow, from fragments that could break off from clot 22. Referring to FIG. 4, as the stent retriever 10 is pulled toward the incision where catheter 16 was introduced, artery 20 will typically widen. Wire 18A may be pulled further back relative to wire 18B, thereby widening out fragment guard 14. Wires 18B and 18A each support a radiopaque marker 40 and 42, respectively, to aid a surgeon in locating the stent retriever during a procedure. The two markers 40 and 42 are spaced apart and mutually distinguishable, to aid a surgeon in determining the orientation of stent retriever 10. In an alternative preferred embodiment, marker 42 is closer to the distal tip of retriever 10.

In one preferred embodiment, wire mesh 12 and spokes 24 are made of nitinol. In another preferred embodiment, mesh 12 and spokes 24 are made of a titanium alloy. In one embodiment, fabric 28 is made of woven strands of expanded polytetrafluoroethylene (ePTFE). In one embodiment, the weave is loose, to permit blood to flow through the interstices of the threads. In still another embodiment, the fabric 28 is made of threads arranged in a circular manner about said spokes, to form a pattern similar to that of a spider web.

Figure 5:
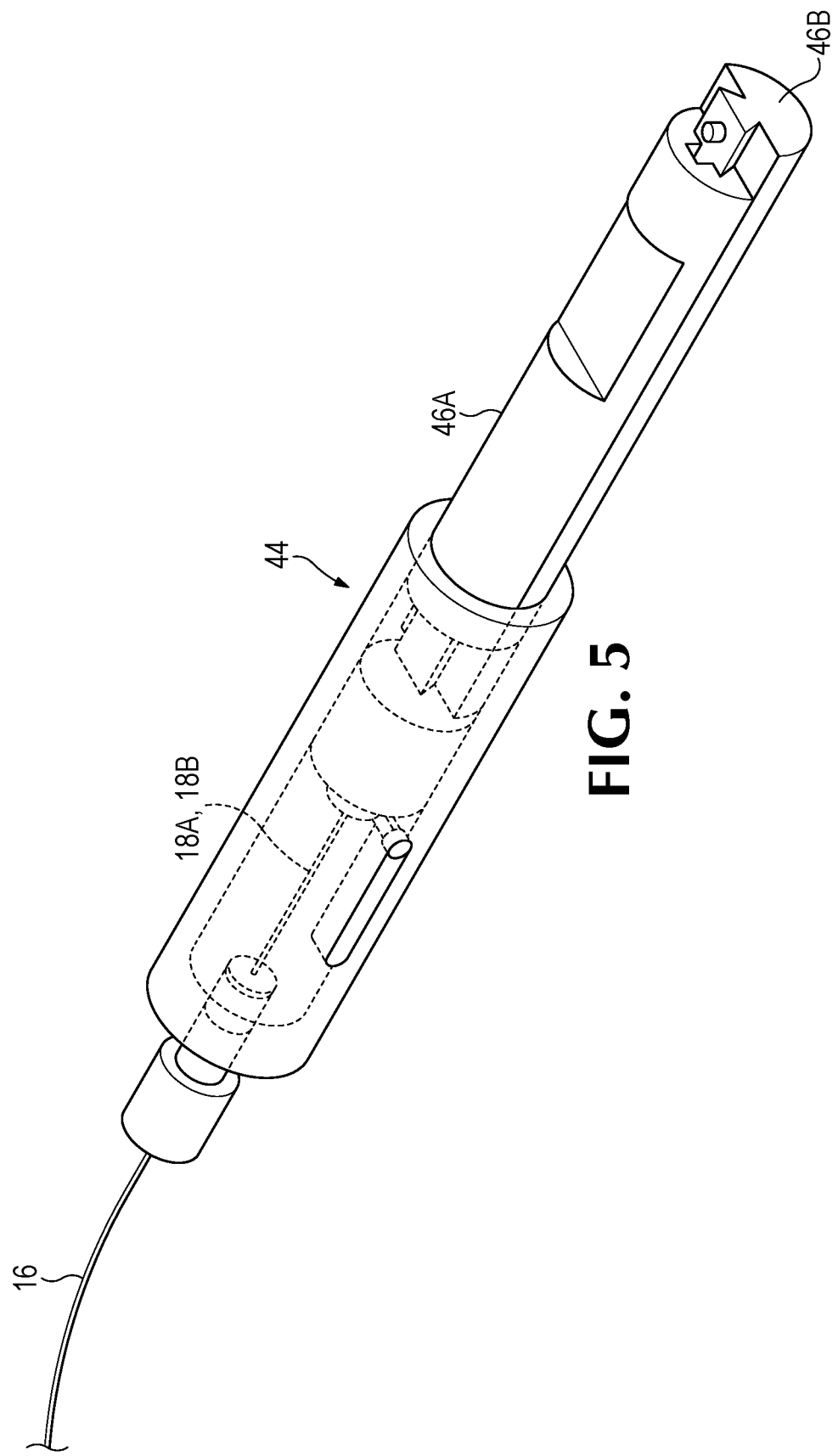
FIG. 5 is an isometric view of a catheter assembly, including a handle assembly, that could be used to control the stent retriever of FIGS. 1-4.

Referring to FIG. 5, catheter 16 is connected to a handle 44, having separately positionable positioners 46A and 46B, for wires 18A and 18B. Handle 44 permits a user to separately move wire 18A and 18B, for deployment and control of the fragment guard 14.

Referring to FIG. 6, in an alternative embodiment of a stent retriever 110, a wire mesh 112 is partially interwoven with a tape 113. Tape 113 provides a further means of retaining clot material, as the retriever is withdrawn from a patient's vasculature. It is more difficult, however, to push the portion of wire mesh 112 covered with this tape 113 through clot material, so typically the surgeon would have to push retriever 110 through the clot material to the point where tape 113 cleared the clot material before deploying retriever 110. Accordingly, various embodiments of retriever 110, with tape 113 interwoven into the most distal 0.1, 0.2, 0.3, . . . 0.8, 0.9 portion of the wire mesh 112 are disclosed here. Tape 113 is, in a preferred embodiment, polytetrafluoroethylene (PTFE) tape. A fragment guard 114 is, in this instance, not made of a woven material, but either of silicone, polyurethane, or a similar soft polymeric material, either without any apertures, or with a set of apertures having diameters, in various embodiments, in the range of 40 to 100 microns.

INDUSTRIAL APPLICABILITY

The invention has industrial applicability in the field of manufacturing devices to aid surgeons in clearing a blood vessel of a clot.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of removing a clot from an artery, comprising:
   (a) providing a stent retriever assembly having a proximal end and a distal end, and including:
      (i) a mesh tube having a distal and proximal end, and being connected to a first wire; and
      (ii) a blood-porous fragment guard mounted at said distal end of said mesh tube, said fragment guard including a central hub and extending radially and proximally from said central hub, and wherein a second wire is connected to said central hub, and wherein when said second wire is pulled proximally relative to said first wire, said hub is pulled proximally, which thereby causes said fragment guard to deploy in expanded form;
   (b) deploying said stent retriever to a proximal side of said clot;
   (c) pushing said stent retriever through said clot;
   (d) pulling said second wire relative to said first wire, thereby widening said fragment guard; and
   (e) pulling said stent retriever proximally to pull material from said clot proximally; wherein said blood clot is in a narrow artery, and wherein as said stent retriever is pulled proximally through the artery, said artery widens and said second wire is pulled further proximally relative to said first wire, causing said fragment guard to widen further to more closely conform to the wider arterial walls.

2. The method of claim 1, wherein said blood clot is in a cranial artery.

3. The method of claim 1, wherein said stent retriever assembly includes a radiopaque element, and wherein during performance of the method location of said stent retriever assembly is monitored by means of said radiopaque element.

4. The method of claim 1, wherein said fragment guard includes spokes, and wherein when said second wire is pulled proximally relative to said first wire, the hub moves proximally and causes said spokes to spread out, which thereby causes said fragment guard to deploy in expanded form.

5. The method of claim 4, wherein said fragment guard, in addition to said spokes, includes threads extending across and between said spokes, to create a finer mesh, better able to hold clot material.

* * * * *